United States Patent [19]

Lang et al.

[11] Patent Number: 4,876,381

[45] Date of Patent: Oct. 24, 1989

[54] NAPHTHALENE DERIVATIVES POSSESSING A RETINOID-TYPE ACTION, PROCESSES FOR THEIR PREPARATION, AND MEDICINAL AND COSMETIC COMPOSITIONS CONTAINING THESE DERIVATIVES

[75] Inventors: Gérard Lang, Saint Gratien; Jean Maignan, Tremblay les Gonesse; Serge Forestier, Claye-Souilly; Serge Restle, Aulnay sous Bois; Alain Lagrange, Chatou; Braham Shroot, Antibes, all of France

[73] Assignee: L'Oreal, Paris, France

[21] Appl. No.: 86,934

[22] Filed: Aug. 18, 1987

[30] Foreign Application Priority Data

Sep. 28, 1984 [LU] Luxembourg .............................. 85558

[51] Int. Cl.$^4$ ............................................. C07C 67/76
[52] U.S. Cl. ......................................... 560/56; 560/64;
560/67; 560/100; 562/461; 562/466; 562/490;
564/84; 564/176; 564/180; 568/27; 568/28;
568/58; 568/326; 568/439; 568/632; 568/732
[58] Field of Search .............................. 560/56, 64, 67;
562/461, 466, 490; 564/84, 176, 180; 568/27,
28, 58, 326, 439, 632, 732

[56] References Cited

PUBLICATIONS

Dawson, Marcia et al., J. Org. Chem. 49 (26), 5265–67, 1984.

Primary Examiner—Paul J. Killos
Attorney, Agent, or Firm—Cushman, Darby & Cushman

[57] ABSTRACT

The invention relates to a compound of the formula (II)

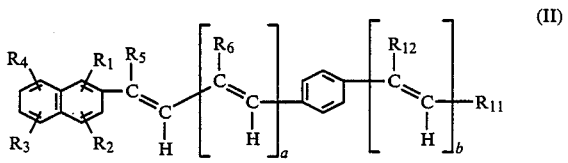

and the corresponding isomers and salts, in which formula:

a and b are integers which independently of one another can assume the values 0 or 1, $R_1$, $R_2$, $R_3$ and $R_4$ represent, independently, a hydrogen atom, a linear or branched $C_1$–$C_6$-alkyl radical or a $C_1$–$C_4$-alkoxy radical, $R_6$ represents a $C_1$–$C_6$-alkyl radical, $R_5$ and $R_{12}$ represent a hydrogen atom or a $C_1$–$C_4$-alkyl radical, with the proviso that $R_5$ cannot represent hydrogen if $a=b=0$ and $R_{11}$ has various meanings.

These compounds have useful dermatological properties.

29 Claims, No Drawings

NAPHTHALENE DERIVATIVES POSSESSING A RETINOID-TYPE ACTION, PROCESSES FOR THEIR PREPARATION, AND MEDICINAL AND COSMETIC COMPOSITIONS CONTAINING THESE DERIVATIVES

The invention relates to new 2-substituted naphthalene derivatives as well as to two processes of preparation by which these new compounds may be obtained. The invention also relates to the use of these new compounds either in cosmetics or in pharmaceutical preparations, in the treatment of dermatological conditions related to a keratinisation disorder (differentiation-proliferation) and in the treatment of dermatological or other conditions involving an inflammatory and/or immuno-allergic component, or as pharmaceutical preparations for the ophthalmic field, especially in the treatment of corneopathies. Moreover, these products can be used in the treatment of cutaneous atopia such as eczema, and in the treatment of rheumatoid psoriasis, as well as in the treatment of disorders due to degeneration of the conjunctive tissue, and of tumours.

The therapeutic action of vitamin A in its acid, aldehyde or alcohol form is well known in dermatology (see, in this context, the publication "EXPERIENTIA", volume 34, pages 1105-1119 (1978)); this action in the treatment of cutaneous proliferations, acne, psoriasis and similar conditions will hereafter be referred to by the generic term "retinoid-type action". It has been found that products having a structure analogous to vitamin A also exhibit a retinoid-type action but that the secondary effect of toxic hypervitaminosis can, in the case of some compounds, be boosted by a smaller factor than the boosting factor of the desired retinoid-type effect (see, in this context, "EUR. J. MED. CHEM.-CHIMICA THERAPEUTICA", January-February 1980, 15, No. 1, pages 9-15; P. Loeliger et al. have, in this latter publication, described a derivative of the formula (I)

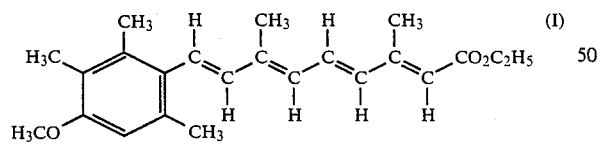

We have previously found that the substituent chain of the compound of the formula (I) can be replaced by a different substituent chain comprising one or two benzene rings, without thereby losing the benefit of the retinoid-type action of these products.

It has now been found, according to the invention, that it is also possible, in the case of a substituent chain containing a benzene ring, by the naphthalene ring without thereby losing the benefit of the retinoid-type action of these compounds.

This invention accordingly provides a new chemical compound corresponding to the general formula (II)

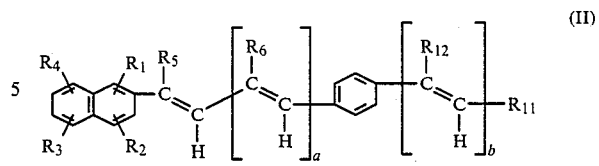

and the corresponding isomers and salts with acids, in which formula:

a and b are independently 0 or 1, $R_1$, $R_2$, $R_3$ and $R_4$, which may be present on one or other of the rings or on both simultaneously, independently represent a hydrogen atom, a linear or branched $C_1$-$C_6$-alkyl radical or a $C_1$-$C_4$-alkoxy radical, $R_6$ represents a $C_1$-$C_6$-alkyl radical, $R_5$ and $R_{12}$ represent a hydrogen atom or a $C_1$-$C_6$-alkyl radical, with the proviso that $R_5$ cannot represent hydrogen if a=b=0 and $R_{11}$ represents a —$COR_9$ group, in which $R_9$ represents (a) a hydrogen atom, a $C_1$-$C_6$-alkyl radical, an amino radical, an optionally substituted arylamino radical or optionally substituted benzylamino radical, the radical of a heterocyclic amine, a $C_1$-$C_6$-alkylamino radical, or a di($C_1$-$C_6$)-alkylamino radical, the alkyl chains of these alkylamino or dialkylamino radicals being optionally substituted by one or more hydroxyl groups and/or interrupted by a hetero-atom and the group —$COR_9$, where it is an amide group, moreover optionally being the amide group of an aminoacid or of glucosamine, or (b) an $OR_{10}$ radical, where $R_{10}$ represents a hydrogen atom, a $C_1$-$C_6$-alkyl radical, a monohydroxy or polyhydroxy$C_2$-$C_6$-alkyl radical or a substituted or unsubstituted aryl or benzyl radical, it also being possible for the radical $OR_{10}$ to be derived from a sugar such as glucose or mannitol, and $R_{11}$ can moreover, if b =0, represent a hydroxyl radical, a $C_1$-$C_4$-alkoxy radical, a $C_1$-$C_6$-alkyl radical, a $C_1$-$C_6$-alkylthio radical, a $C_1$-$C_6$-alkylsulphinyl radical, a $C_1$-$C_6$-alkylsulphonyl radical or a sulphonamide radical of the formula (III)

where $R_7$ represents a $C_1$-$C_6$-alkyl radical and $R_8$ either a hydrogen atom or a $C_1$-$C_6$-alkyl radical, and $R_{11}$ can, finally, represent a radical of the formula (IV)

in which formula $R_8$ has the meaning given above.

Amongst the $C_1$-$C_6$-alkyl radicals which are particularly useful in respect of the radicals $R_1$ to $R_{12}$ mentioned above there may be mentioned the methyl, ethyl, isopropyl, butyl and t-butyl radicals and preferably, for $R_1$, $R_2$, $R_4$, $R_5$, $R_6$ and $R_{12}$, the methyl radical.

Among the substituted or unsubstituted aryl radicals which are particularly useful in respect of the radicals $R_9$ and $R_{10}$, the phenyl radical, optionally substituted by a halogen atom or a hydroxyl or $C_1$-$C_6$-alkoxy group is preferred.

The compounds of the formula (II) can be in the form of their salts; these can be either zinc salts or alkali metal or alkaline earth metal salts or salts of an organic amine if the compounds contain at least one free acid group, or salts of an inorganic or organic acid, especially the hydrochloride, hydrobromide or citrate, if the compounds contain at least one amine group.

The invention also relates to the isomers of the compounds of the formula (II) and to their salts.

Among the preferred compounds there may be mentioned those corresponding to the formula (II), in which $R_1$, $R_2$, $R_3$, $R_4$, $R_5$, $R_6$, $R_{12}$, a and b have the values or meanings indicated above and in which $R_{11}$ denotes —$COR_9$, with $R_9$ representing an amino, alkylamino, dialkylamino or arylamino radical, which radicals may optionally be substituted, or representing the —$OR_{10}$ radical, $R_{10}$ being defined as above.

Among the more particularly preferred compounds of the formula (II) there may be mentioned those represented by the following formula (A)

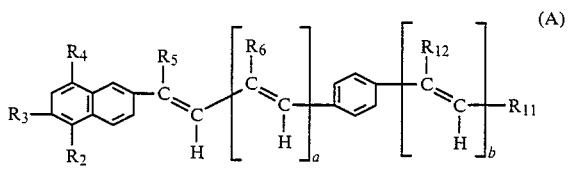

in which:

$R_5$, $R_6$, $R_{12}$, a and b are defined as above, $R_3$ denotes a $C_1$-$C_4$-alkoxy radical, $R_2$ and $R_4$ each represent a $C_1$-$C_4$-alkyl radical $R_{11}$ assumes the meaning —$COR_9$, with $R_9$ representing an amino, alkylamino or dialkylamino radical, an optionally substituted arylamino or benzylamino radical, or the radical of the heterocyclic amine, of an aminoacid or of glucosamine, the alkyl chain of the alkylamino and dialkylamino radicals containing from 1 to 6 carbon atoms and being optionally substituted by one or more hydroxyl groups and/or interrupted by a hetero-atom, or $R_{11}$ represents an —$OR_{10}$ radical, $R_{10}$ being defined as above.

The invention also provides a first process for the preparation of the compounds of the formula (II). According to this first process, the synthesis is carried out by a Witting reaction. The process accordingly comprises, in the last stage, the reaction, in a basic medium, of an aldehyde OCHR with a substituted or unsubstituted 2-(1'-triphenylphosphonium-alkyl)-naphthalene, in accordance with the reaction

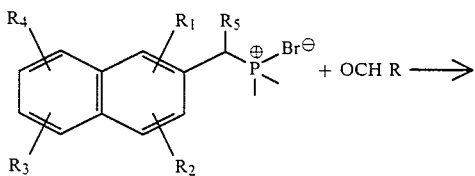

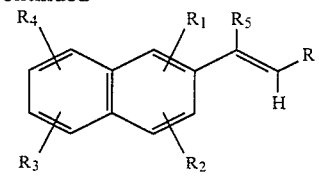

R representing the substituent chain of the formula (V)

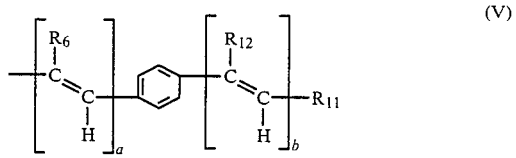

where $R_6$, $R_{12}$, $R_{11}$, a and b have the meanings indicated above.

The invention also relates to a second process for the preparation of the new compounds of the formula (II) according to which a modified Witting reaction is used. According to this second process, a 2-acyl-naphthalene of the formula (VI):

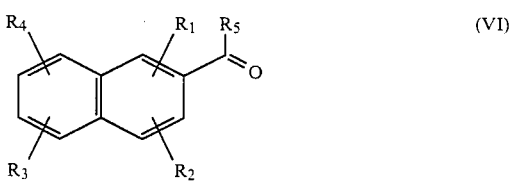

is reacted with a phosphonate derivative of the formula (VII)

or with a triphenylphosphonium salt of the formula (VIII)

$$R-CH_2-P+(C_6H_5)_3X^{31}  \qquad (VIII)$$

in which formulae $R_1$, $R_2$, $R_3$, $R_4$, $R_5$ and R have the meanings given above, X represents a halogen atom and R' represents a $C_1$-$C_4$-alkyl radical.

In the first process of preparation mentioned above, the 2-(1'-triphenylphosphonium-alkyl)-naphthalene salts are known compounds which can advantageously be obtained as follows:

(a) in a first stage, the naphthalene nucleus is acylated by a Friedel-Craft reaction, (b) in a second stage, the acylnaphthalene obtained is reduced with sodium borohydride to give the corresponding alcohol, (c) in a third stage, the said alcohol is reacted with phosphorus tribromide to give the 2-(1'-bromo-alkyl)-naphthalene and (d) in a fourth stage, approximately one equivalent of triphenylphosphine is reacted with the latter to give the desired salt.

The whole of this preparation can be represented by the following scheme of operation:

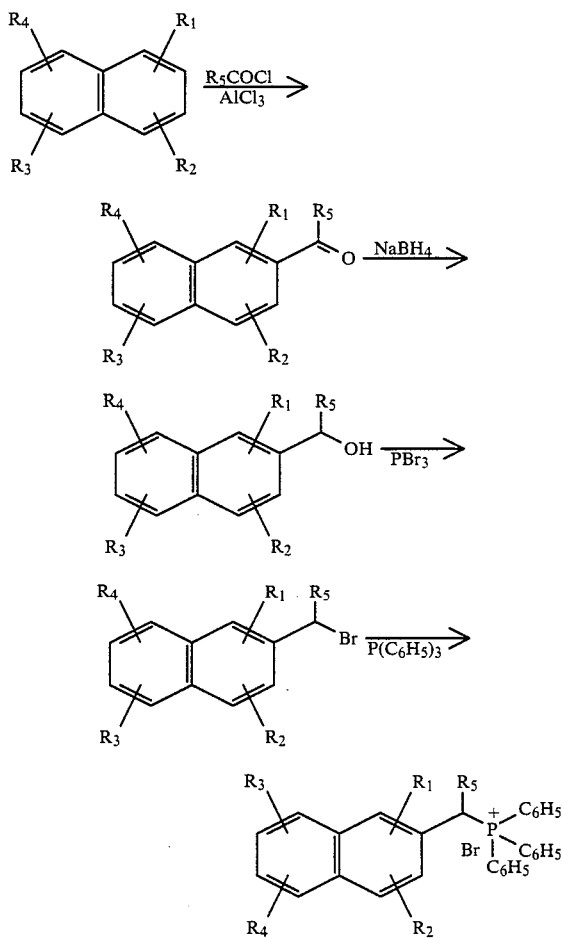

The aldehydes which are used in the first process of preparation, mentioned above, are commercial products or known products which can be prepared in accordance with known methods.

The compound of the formula (II) are obtained in the form of a cis/trans mixture which can, if desired, be separated in a manner known per se into the pure cis and trans compounds.

According to the invention, it has been found that the compounds of the formula (II) have a retinoidtype action and are particularly suitable for the treatment of dermatological conditions related to a keratinisation disorder (differentiation-proliferation) as well as dermatological or other conditions which involve an inflammatory and/or immuno-allergic component, in particular for treatment of common acne, blackheads, polymorphic acne, senile acne, acne caused by exposure to sunlight, by medicinal treatment or by working conditions, extensive and/or severe forms of psoriasis and other keratinisation disorders, and in particular ichtyoses and ichtyosiform conditions, Darier's disease, palmo-plantar keratoderma, leucoplakia and leucoplakiform conditions, lichen planus and all severe or extensive dermatological proliferations, whether benign or malignant. They are also active against rheumatoid psoriasis. These compounds can also be used in the treatment of cutaneous atopya such as eczema. Finally, they are used in the ophthalmic field, especially for the treatment of corneopathia. They can be indicated in dystrophic vesicular epidermolyses and in molecular pathology of collagen. They are also indicated in carcinomas induced by ultraviolet (solar carcinogenesis), in verruciform epidermodysplasia and in related forms.

These compounds exhibit a good activity in the ornithine decarboxylase (ODC) inhibition test after induction by tape stripping in the hairless rat (Dermatologica 169, No. 4 (1984) "A Rapid and Simple Test System for the Evaluation of the Inhibitory Activity of Topical Retinoids on Cellotape Stripping Induced ODC Activity in the Hairless Rat" M. BOUCLIER et al.). This test is accepted as a measure of the action of retinoids in connection with cellular proliferation phenomena.

The compounds according to the invention exhibit an excellent comedolytic activity in the Rhino mouse test described by BONNE et al. in International Journal of Cosmetic Science 3, 23-28 (1981). This experiment is carried out on the skin of the hairless Rhino mouse, proposed as a screening model for comedolytic agents by VAN SCOTT in 1972, and based on the histological appearance. In this test, the compound of Example 11 below has proved very active at a concentration of 0.1% in acetone.

The invention thus also concerns the medicinal compositions containing the compounds of the formula (II).

The present invention thus also relates to a new medicinal composition, intended in particular for the treatment of the abovementioned conditions, and characterised in that it comprises at least one compound of the formula (II) and/or one of its isomers and/or one of its salts, in a pharmaceutically acceptable base.

If the compounds according to the invention are used topically, it is found that they exhibit a good activity over a very broad range of dilution; in particular, concentrations of the active compound or compounds ranging from 0.0005% to 2% by weight can generally be used. It is of course possible to use higher concentrations if this should become necessary for a particular therapeutic application; however, the preferred concentrations of active principle are fom 0.002% to 1% by weight.

The topical compositions are advantageously in the form of unguents, gels, creams, ointments, powders, dyeing compositions, solutions, suspensions, emulsions, lotions, sprays, adhesive plasters and impregnated pads. The compounds according to the invention can be mixed with inert non-toxic, generally liquid or pasty, bases suitable for topical treatment.

The compounds according to the invention can also be used enterally. Orally, the compounds according to the invention are suitably administered at the rate of about 2µg to 2 mg per day per kg of body weight; an excessive posology can reveal itself as a hypervitaminosis A, recognisable from its symptoms, and can involve the danger of liver toxicity, necessitating biological control of the liver function. The required dose can be administered in one or more portions. For oral administration, suitable forms are, for example, tablets, pills, dragees, syrups, suspensions, emulsions, solutions, powders and granules; a preferred method of administration consists in using pills containing method of administration consists in using pills containing from 0.1 mg to about 1 mg of active substance.

The compounds according to the invention can also be administered parenterally in the form of solutions or suspensions for intravenous or intramuscular perfusions or injections. In that case, the compounds according to the invention are generally administered at the rate of about 2 μg to 2 mg per day per kg of body weight; a preferred method of administration consists of using solutions or suspensions containing approximately from 0.01 mg to 1 mg of active substance per ml.

Where the compounds according to the invention are used for ocular administration, they are advantageously in the form of solutions or of powders to be diluted to form eye drops.

The pharmaceutically acceptable base can contain water, gelatin, lactose, starch, talc, liquid petrolatum, gum arabic, polyalkylene glycols or magnesium stearate, for example. The tablets, powders, dragees, granules or pills can contain binders, fillers or pulverulent bases. The solutions, creams, suspensions, emulsions or syrups can contain diluents, solvents or thickeners.

The compounds of the formula (II) according to the invention, their isomers and their salts, also find application in the cosmetics field, in particular in body hygiene and hair hygiene, and especially in the treatment of acne, dry skin, seborrhoea and loss of hair, for encouraging fresh growth of hair, for the protection against, and treatment of, adverse effects of sunlight and in the treatment of physiologically dry skin.

The present invention thus also relates to a new cosmetic composition characterised in that it comprises, in a cosmetically acceptable base, at least one compound of the formula (II) and/or one of its isomers and/or one of its salts, this composition being in the form of a lotion, gel, cream, soap, shampoo or the like.

The concentration of the compound or compounds of the formula (II) and/or of isomers and/or salts of this compound or these compounds in the said cosmetic compositions is generally 0.0005 to 2% by weight and preferably 0.01 to 1% by weight relative to the total weight of the composition.

In the treatment of the abovementioned disorders, the compounds according to the invention, used in the compositions defined above, act by increasing the follicular epithelial production of non-adhering cells, thus dislodging, and causing the loss of, the contents of the acne blackhead. These compounds reduce the size of the sebaceous glands and partially inhibit the secretion of sebum.

The compositions according to the invention can contain inert additives and also pharmacodynamically or cosmetically active additives and in particular moisturising agents such as thiamorpholinone and its derivatives or urea, antiseborrhoeic agents or anti-acne agents such as those described in French Patents Nos. 1,472,021, 1,505,874, 1,560,250, 2,002,461, 2,035,799, 2,011,940, 2,060,407, 2,126,996, 2,133,991, 2,133,992, 2,139,876, 2,158,018, 2,296,406, 2,428,436, 2,446,277, 2,447,189 and 2,468,362 and in U.S. Pat. Nos. 2,332,418 and, in particular, S-carboxymethylcysteine, S-benzylcysteamine, their salts and their derivatives, thioxolone or benzoyl peroxide, antibiotics, such as erythromycin and its esters, for example those described in U.S. Pat. Nos. 2,862,921 or French Patent application No. 85/05785, neomycin, tetracyclines or 4,5-polymethylene-isothiazolin-3-ones, such as are described in French Patent No. 2,492,376, agents which assist the fresh growth of hair, such as "Minoxidil" (2,4-diamino-6-piperidino-pyrimidine-3-oxide) and its derivatives, diazoxide (3-chloromethyl-benzo-1,2,4-thiadiazine-1,1-dioxide), phenytoin (5,5-diphenyl-imidazolidine-2,4-dione), oxapropanium iodide or anthraline and its derivatives, anti-inflammatory agents (of a steroid or nonsteroid type), carotenoids and especially β-carotene, and anti-psoriasis agents such as eicosa-5,8,11,14-tetraynoic acid and eicosa-5,8,11-triynoic acid, their esters and their amides, anthraline and its derivatives, such as those described in French Patent Nos. 2,113,952, 2,492,372, 2,492,373, 2,495,934 and 2,499,556 or French Patent applications Nos. 84/09203 and 84/10324 or U.S. Patent No. 4,299,846, and naphthalene and naphthoquinone derivatives such as those described in U.S. Pat. Nos. 4,299,478, European Patent No. 7985 or J.I.D. 84 (4) 358 (1985).

The compositions according to the invention can also contain flavourings, preservatives, stabilisers, moisture regulators, pH regulators, osmotic pressure modifiers, emulsifiers, UV-A and UV-B filters such as those described in French Patents Nos. 1,179,387 or 2,528,420 and antioxidants such as α-tocopherol, butylhdroxyanisole or butylhydroxytoluene.

In order that the subject of the invention is slightly better understood, several embodiments will now be described.

Examples A and B, which are described below, do not form part of the invention and relate to the preparation of, respectively, 6,7-dimethyl-2-(1'-triphenylphosphonium-ethyl)-naphthalene bromide and 5,8-dimethyl-6-methoxy-2-(1'-triphenylphosphonium-ethyl)-naphthalene bromide, which are used as starting materials for the examples of the preparation of the compounds of the formula (II) according to the invention.

The Preparation Examples 1 to 14 lead to compounds according to the invention which all have a trans-structure.

EXAMPLE A

Preparation of 6,7-dimethyl-2-(1'-triphenylphosphoniumethyl)-naphthalene bromide First stage: Preparation of 2-acetyl-6,7-dimethyl-naphthalene 100 g of 2,3-dimethyl-naphthalene are added in small portions, over the course of about one hour, to a mixture of 94 g of aluminium chloride (10.70 moles) and 50 cm³ of acetyl chloride (0.70 mole) in one litre of methylene chloride, with stirring, under an inert atmosphere. Stirring is continued for 5 hours after the end of the addition. The reaction mixture is then poured into water, with stirring.

The organic phase is decanted, washed until the wash waters are neutral and dried over magnesium sulphate.

Evaporation of the methylene chloride on a rotary evaporator gives, after drying and recrystallisation from hexane, 65 g of 2-acetyl-6,7-dimethyl-naphthalene.

Second stage: Preparation of 6,7-dimethyl-2-(1'-hydroxyethyl)-naphthalene

Two equivalents of sodium borohydride are added, a little at a time, to a solution of 50 g of 2-acetyl-6,7-dimethyl-napthalene (0.26 mole) in 500 cm³ of methanol at ambient temperature and under an inert atmosphere, with stirring. The temperature is kept below 50° C. by means of an ice bath. One hour after the end of the addition, the whole of the starting material has been converted.

400 cm³ of water is then added to the mixture. The methanol is evaporated under reduced pressure. The aqueous phase is then neutralised by adding hydrochloric acid and is thereafter extracted with ether. The organic phase is washed, dried over magnesium sulphate and concentrated. 45 g of a viscous liquid are obtained, the nuclear magnetic resonance spectrum of which corresponds to the expected structure.

Third stage: Preparation of 2-(1'-bromoethyl)-6,7-dimethylnaphthalene 36 cm³ of phosphorus tribromide are added dropwise, at ambient temperature, under an inert atmosphere, to a solution of 50 g of the alcohol prepared in the second stage, in 500 cm³ of methylene chloride.

After three hours' stirring at ambient temperature, the reaction mixture is left overnight. The excess reagent is destroyed by adding 200 cm³ of water. The organic phase is decanted, washed repeatdly with water, dried over sodium sulphate and then evaporated under reduced pressure. This gives, after prolonged drying, 60 g of 2-(1'-bromoethyl)-6,7-dimethyl-naphthalene.

Fourth stage: Preparation of 6,7-dimethyl-2-(1'-triphenylphosphoium-ethyl)-naphthalene bromide 1.1 equivalents of triphenylphosphine are added, at ambient temperature, to a solution of 50 g of the compound prepared in the third stage, in 300 cm³ of toluene. The mixture is then heated to the boiling point of toluene for 48 hours, with stirring. Triphenylphosphonium bromide precipitates at the rate at which it is formed. At the end of the reaction, it is filtered off and then dried.

This gives 90 g of 6,7-dimethyl-2-(1'-triphenylphosphonium-ethyl)-naphthalene bromide.

EXAMPLE B

Preparation of 5,8-dimethyl-6-methoxy-2-(1'-triphenylphosphonium-ethyl)-naphthalene bromide First stage: Preparation of 2-acetyl-5,8-dimethyl-6-methoxy-naphthalene This product is prepared from 1,4-dimethyl-3-methoxy-naphthalene, which is synthesised in accordance with a method described by M. FETIZON and N.T. ANH, Bull. Soc. Chim. Fr, 3028, 1965.

A solution containing a mixture of 65 g of 1,4-dimethyl-3-methoxy-naphthalene and 24.8 cm³ of acetyl chloride in 300 cm³ of anhydrous methylene chloride is introduced dropwise into a suspension of 70 g of anhydrous aluminium chloride in 800 cm³ of methylene chloride at 0° C. under an inert atmosphere, with stirring. Upon completion of the addition, the reaction mixture is stirred for 4 hours at ambient temperature and is then left overnight. The following day, it is poured onto crushed ice and extracted three times with 250 cm³ of methylene chloride. The organic phases are combined, washed with aqueous bicarbonate solution and then with water. They are dried over magnesium sulphate and then concentrated to about 200 cm³. 25.5 g of crystalline product are isolated by cooling the solution. Hexane is added to the filtrate and an additional 10 g of product are isolated. The unconverted 1,4-dimethyl-3-methoxy-naphthalene remains in solution.

The 2-acetyl-5,8-dimethyl-6-methoxy-naphthalene thus isolated is a white powder which melts at 118° C. Its ¹H nuclear magnetic resonance spectrum corresponds to the expected structure.

Second stage: Preparation of 5,8-dimethyl-6-methoxy-2-(1'-hydroxyethyl)-naphthalene 14.2 g of sodium borohydride are added, in small portions, to a suspension of 50 g of 2-acetyl-5,8-dimethyl-6-methoxy-naphthalene in one litre of methanol at 0° C., with stirring, in such a way that the temperature does not exceed 5° C. Stirring is then continued at this temperature for 4 hours. The reaction mixture is left at ambient temperature overnight and is then poured onto crushed ice. The methanol is removed by evaporation in vacuo. The aqueous phase is acidified by adding 2 N hydrochloric acid. The precipitate formed is filtered off and then dried. This gives 48 g of 5,8-dimethyl-6-methoxy-2-(1'-hydroxyethyl)-naphthalene in the form of white crystals of melting point 78° C. The ¹H nuclear magnetic resonance spectrum corresponds to the expected structure.

Third stage: Preparation of 5,8-dimethyl-6-methoxy-2-(1'-triphenylphosphonium-ethyl)-naphthalene bromide 19.7 cm³ of 48% strength hydrobromic acid are added dropwise to a mixture of 40 g of 5,8-dimethyl-6-methoxy-2-(1'-hydroxyethyl)-naphthalene and 45.6 g of triphenylphosphine in 1.5 litres of methanol at ambient temperature, with stirring. Upon completion of the addition, the mixture is stirred for a further five hours and is then left overnight.

The methanol is removed under reduced pressure. The product obtained in the form of a viscous liquid is dissolved in the minimum amount of methylene chloride. The solution is then poured into ice-cooled ethyl ether, with stirring. The expected salt crystallises. It is filtered off and dried. 83 g of 5,8-dimethyl-6-methoxy-2-(1'-triphenylphosphonium-ethyl)-naphthalene bromide are obtained.

This material consists of pale yellow crystals melting, with decomposition, at 145° C.

The ¹H nuclear magnetic resonance spectrum corresponds to the expected structure.

EXAMPLE 1

Preparation of 2-(4'-methyl-β-methyl-styryl)-naphthalene

A mixture of 7.5 g of 2-(1'-triphenylphosphonium)-ethyl-naphthalene bromide (0.015 mole), 2 cm³ of para-toluylaldehyde (1.1 equivalents) and 4.2 g of potassium carbonate (2 equivalents) in 75 cm³ of isopropanol is heated to a temperature of about 80° C., with stirring. The course of the reaction is followed by plate chromatography. Three hours' heating are required to convert the majority of the starting material. The reaction mixture is filtered hot. The product crystallises upon cooling of the filtrate. It is filtered off, dissolved in the minimum amount of methylene chloride and deposited, in solution, on a silica gel column. After having concentrated the methylene chloride elution phases, 2.5 g of white crystals, of melting point 109° C., are obtained.

| Elementary analysis: | | |
| --- | --- | --- |
|  | C | H |
| Calculated for $C_{20}H_{18}$ | 92.98 | 7.02 |
| Found | 92.67 | 7.04 |

EXAMPLE 2

Preparation of 2-(4'-methoxy-β-methyl-styryl)-naphthalene

A mixture of 5.5 g of 2-(1'-triphenylphosphonium)-ethyl-naphthalene bromide (0.011 mole) in 1.6 cm³ of para-anisaldehyde (0.013 mole) and 3.8 g of potassium carbonate (2.5 equivalents) in 50 cm³ of isopropanol is heated to a temperature of about 80° C. for 8 hours, during which time the majority of the starting material is converted.

The reaction mixture is filtered hot and the potassium carbonate is rinsed with isopropanol. The filtrate is cooled to 0° C. A crystalline product is filtered off and dissolved in methylene chloride, and the solution obtained is deposited on a silica gel column. After the elution phases have been concentrated, 2 g of 2-(4'-methoxy-β-methyl-styryl)-naphthalene melting at 141° C. are obtained.

| Elementary analysis: | | |
| --- | --- | --- |
| | C | H |
| Calculated for $C_{20}H_{18}O$ | 87.56 | 6.61 |
| Found | 87.02 | 6.62 |

EXAMPLE 3

Preparation of 2-(4'-methylthio-β-methyl-styryl)naphthalene

A mixture of 25 g of 2-(1'-triphenylphosphonium)-ethyl-naphthalene bromide, 7.2 cm³ of 4-methylthio-benzaldehyde and 13.8 g of potassium carbonate in 300 cm³ of isopropanol is heated at 80° C. for three hours and after evaporation of the solvent a solid is obtained, which is extracted repeatedly with methylene chloride. After evaporation of the solvent to dryness under reduced pressure, 10.7 g of a white solid are obtained and this is recrystallised from toluene. 6.5 g of pure 2-(4'-methylthio-β-methyl-styryl)-naphthalene melting at 161° C. are thus isolated.

| Elementary analysis: | | | |
| --- | --- | --- | --- |
| | C | H | S |
| Calculated for $C_{20}H_{18}S$ | 82.71 | 6.25 | 11.04 |
| Found | 83.08 | 6.29 | 10.57 |

EXAMPLE 4

Preparation of 2'-(4'-methylsulphonyl-β-methyl-styryl)naphthalene

4-Methylsulphonyl-benzaldehyde is prepared in a first stage.

2.1 equivalents of 30% strength hydrogen peroxide are added dropwise, with stirring, to a solution of 5 cm³ of 4-methylthio-benzaldehyde in 50 cm³ of formic acid. The reaction is exothermic and the temperature rises to 75° C. Stirring is continued for half an hour after the completion of the addition. The expected sulphone crystallises at ambient temperature. It is filtered off, washed repeatedly with water and then dried.

4.5 g of pure 4-methylsulphonyl-benzaldehyde are thus obtained.

A mixture of 2.2 g of this sulphone, 5 g of 2-(1'-triphenylphosphonium)-ethyl-naphthalene bromide and 2.5 g of potassium carbonate in 50 cm³ of isopropanol is heated to a temperature of 80° C. for three hours. The reaction mixture is filtered. The potassium carbonate is extracted with methylene chloride. After evaporation of the methylene chloride, 1.5 g of crude product are obtained. The isopropanol from the filtrate is cooled. The product crystallises; it is filtered off and dried. 1 g of product is thus obtained.

2.5 g of 2-(4'-methylsulphonyl-β-methyl-styryl)naphthalene are purified by chromatography on a silica gel column. After concentration of the elution phases, 1.9 g of white crystals melting at 146° C. are obtained.

| Elementary analysis: | | | | |
| --- | --- | --- | --- | --- |
| | C | H | 0 | S |
| Calculated for $C_{20}H_{18}O_2S$ | 74.50 | 5.63 | 9.93 | 9.94 |
| Found | 74.59 | 5.70 | 9.65 | 9.40 |

EXAMPLE 5

Preparation of 2-(4'-methylsulphinyl-β-methyl-styryl)naphthalene 1.1 equivalents of meta-chloroperbenzoic acid are added, in small portions, with stirring, to a solution of 2 g of 2-(4'-methylthio-β-methyl-styryl)-naphthalene, prepared according to Example 3 in 80 cm³ of methylene chloride, at ambient temperature. The reaction mixture is then left overnight and is thereafter poured onto 200 cm³ of water.

The aqueous phase is neutralised with sodium bicarbonate, while stirring.

The organic phase is decanted, dried over magnesium sulphate and filtered.

The methylene chloride is evaporated in vacuo and the product is deposited on a silica gel chromatography column. After concentration of the elution phases (methylene chloride and a 1/1 methylene chloride/ethyl acetate mixture), 1.6 g of white crystals, of melting point 157° C., are obtained.

| Elementary analysis: | | |
| --- | --- | --- |
| | C | H |
| Calculated for $C_{20}H_{18}OS$ | 78.40 | 5.92 |
| Found | 78.80 | 6.08 |

EXAMPLE 6

Preparation of ethyl 4-[2-all-trans-(2'-naphthyl)-propenyl]-cinnamate

A mixture of 10 g of 2-(1'-triphenylphosphonium-ethyl)-naphthalene bromide, 4 g of ethyl 4-formyl-cinnamate and 10 g of potassium carbonate in 100 cm³ of isopropanol is heated to the boiling point of isopropanol.

After four hours' refluxing, the mixture is filtered hot and the solid is washed with methylene chloride. The filtrate is concentrated under reduced pressure. The solid obtained is recrystallised twice from a hexane/ethyl acetate mixture. 3.5 g of ethyl 4-[2-trans-(2'-naphthyl)-propenyl]-cinnamate are obtained in the form of white crystals, of melting point 132°–133° C.

The ¹H nuclear magnetic resonance spectrum at 250 MHz agrees with the all-trans structure of the product.

EXAMPLE 7

Preparation of
2-(4'-ethoxycarbonyl-β-methyl-styryl)naphthalene 31 g of diethyl 4-ethoxycarbonyl-benzylphosphonate and a few drops of 1,4,7,10,13-pentaoxa-cyclopentadecane are added to a suspension of 5.5 g of sodium hydride in 100 cm$^3$ of tetrahydrofuran. The mixture is stirred at 45° C. for one hour and 17 g of 2-acetyl-naphthalene are then added. It is kept at 45° C. for three hours, allowed to cool, then diluted with dichloroethane. The insoluble matter is filtered off and the filtrate is evaporated under reduced pressure. The residue is recrystallised twice from ethanol. 14 g of the expected product are obtained.
Melting point: 96° C.

| UV spectrum: | $\lambda$max = 315 nm | (chloroform) |
| --- | --- | --- |
| | $\epsilon$ = 27100 | |
| | $\lambda$max = 275 nm | (chloroform) |
| | $\epsilon$ = 26000 | |

| Elementary analysis: | | | |
| --- | --- | --- | --- |
| | C | H | O |
| Calculated for $C_{22}H_{20}O_2$ | 83.51 | 6.37 | 10.11 |
| Found | 83.58 | 6.43 | 10.09 |

EXAMPLE 8

Preparation of
2-(4'-carboxy-β-methyl-styryl)-naphthalene 10 g of potassium hydroxide are dissolved in 50 cm$^3$ of water and 200 cm$^3$ of ethanol. 10 g of the compound prepared in Example 7 are added and the reaction mixture is heated under reflux for one hour, cooled and then acidified. The precipitate is filtered off and the insoluble matter is recrystallised from acetic acid. 7 g of the expected product are obtained.
Melting point: 238° C.

| UV spectrum: | $\lambda$max = 304 nm | (methanol) |
| --- | --- | --- |
| | $\epsilon$ = 25600 | |

| Elementary analysis: | | | |
| --- | --- | --- | --- |
| | C | H | O |
| Calculated for $C_{20}H_{16}O_2$ | 83.31 | 5.59 | 11.10 |
| Found | 83.12 | 5.59 | 11.14 |

EXAMPLE 9

Preparation of
2-[4-(4'-methoxycarbonyl-phenyl)-3-methyl-butadienyl]-naphthalene 32.6 g of diethyl 3-(4'-methoxycarbonyl-phenyl)-3-methyl-prop-2-enyl-phosphonate are added to a suspension of 5 g of sodium hydride in 100 cm$^3$ of tetrahydrofuran containing a few drops of 1,4,7,10,13-pentaoxa-cyclopentadecane. The temperature rises to 35° C. 15.6 g of 2-naphthaldehyde dissolved in 100 cm$^3$ of tetrahydrofuran are added dropwise, with stirring, while keeping the temperature at about 30° C. The mixture is stirred for two hours and is then neutralised with dilute hydrochloric acid. The expected product precipitates. The precipitate is filtered off and recrystallised from methylene chloride. 3 g of yellow crystals are obtained.
Melting point: 182° C.

| UV spectrum: | $\lambda$max = 347 nm | (chloroform) |
| --- | --- | --- |
| | $\epsilon$ = 47000 | |

| Elementary analysis: | | | |
| --- | --- | --- | --- |
| | C | H | O |
| Calculated for $C_{23}H_{20}O_2$ | 84.12 | 6.14 | 9.74 |
| Found | 84.20 | 6.18 | 9.50 |

EXAMPLE 10

Preparation of
2-[4-(4'-carboxyphenyl)-3-methylbuta-dienyl]-naphthalene

A suspension of 2.5 g of the compound obtained in Example 9 in 250 cm$^3$ of ethanol and 100 cm$^3$ of 3 N sodium hydroxide is heated under reflux for 3 hours. It is allowed to cool and is diluted with water, and the ethanol is evaporated under reduced pressure. The residue is acidified with hydrochloric acid and the precipitate is then filtered off. After recrystallisation from acetic acid, 1.4 g of the expected product are obtained.
Melting point: 265° C.

| UV spectrum: | $\lambda$max = 338 nm | (dimethylsulphoxide + methanol) |
| --- | --- | --- |
| | $\epsilon$ = 50700 | |

| Elementary analysis: | | | |
| --- | --- | --- | --- |
| | C | H | O |
| Calculated for $C_{22}H_{18}O_2$ | 84.05 | 5.77 | 10.18 |
| Found | 84.12 | 5.81 | 10.15 |

EXAMPLE 11

Preparation of
trans-N-ethyl-4-[2-(5,8-dimethyl-6-methoxy-2-naphthyl)-propenyl]-benzamide A suspension of 15 g of the triphenylphosphonium salt (prepared according to Example B) in 80 cm$^3$ of isopropanol containing 9.3 g of potassium bicarbonate is heated to 80° C., with stirring, for one hour. Thereafter 4.8 g of N-ethyl-4-formyl-benzamide are introduced, with exclusion of light, and the reaction mixture is then heated under reflux for 20 hours. At a temperature of about 80° C., the mixture is then passed over a silica gel filter. The filter is washed with boiling isopropanol. The isopropanol is removed by evaporation in vacuo.

The product obtained is dissolved in 250 cm$^3$ of acetonitrile heated to the boil. On cooling, N-ethyl-4-[2-(5,8-dimethyl-6-methoxy-2-naphthyl)-propenyl]-benzamide crystallises. It is filtered off and dried. 6 g of white crystals, melting point 185° C., are obtained. The $^1$H nuclear magnetic resonance spectrum at 250 MHz corresponds to the

| Elementary analysis: | | | | |
|---|---|---|---|---|
| | C | H | N | O |
| Calculated for $C_{25}H_{27}NO_2$ | 80.39 | 7.29 | 3.75 | 8.57 |
| Found | 80.14 | 7.28 | 3.67 | 8.85 |

EXAMPLE 12

Preparation of methyl trans-4-[2-(5,8-dimethyl-6-methoxy-2-naphthyl)-propenyl]-benzoate 4.43 g of methyl 4-formyl-benzoate are added, in small portions, to a suspension of 15 g of the triphenylphosphonium salt (prepared according to Example B) and 9.3 g of potassium bicarbonate in 250 cm³ of isopropanol at a temperature of about 80° C., with exclusion of light and while stirring. The mixture is heated under reflux for 6 hours. The boiling solution is then passed over a silica gel filter. The filter is rinsed with methylene chloride. The isopropanol and methylene chloride filtrates are combined and concentrated to the point where the expected ester begins to crystallise. After cooling, the crystals are filtered off and dried. 4.5 g of methyl trans-4-[2-(5,8-dimethyl-6-methoxy-2-naphthyl)-propenyl]-benzoate are obtained in the form of white crystals of melting point 128° C.

The ¹H nuclear magnetic resonance spectrum at 60 MHz corresponds to the expected structure.

EXAMPLE 13

Preparation of ethyl trans-4-[2-(5,8-dimethyl-6-methoxy-2-naphthyl)-propenyl]-benzoate A few drops of the crown ether 1,4,7,10,13-pentaoxacyclopentadecane are added to a suspension of 0.85 g of sodium hydride in 100 cm³ of anhydrous tetrahydrofuran, stirred in the absence of light and under an inert atmosphere; thereafter a mixture of 3.5 g of 2-acetyl-5,8-dimethyl-6-methoxy-naphthalene and 4.5 g of 4-ethoxycarbonyl-benzylphosphonate is introduced rapidly.

The whole is heated for three hours under reflux. The reaction mixture, when it has reached ambient temperature, is poured onto ice and then extracted with methylene chloride. The organic phase is decanted, washed with water, dried over magnesium sulphate and then concentrated.

The expected product is purified by passing it over a silica gel column and eluting with a 95/5 hexane/ethyl ether mixture. After evaporation of the eluant, 2.5 g of product, containing traces of cis-isomer, are isolated.

After recrystallisation from isopropyl ether, 1.5 g of ethyl trans-4-[2-(5,8-dimethyl-6-methoxy-2-naphthyl)-propenyl]-benzoate are isolated in the form of crystals melting at 94° C.

| Elementary analysis: | | | |
|---|---|---|---|
| | C | H | O |
| Calculated for $C_{25}H_{26}O_3$ | 80.18 | 6.99 | 12.81 |
| Found | 80.19 | 7.02 | 12.86 |

EXAMPLE 14

Preparation of trans-4-[2-(5,8-dimethyl-6-methoxy-2-naphthyl)-propenyl]-benzoic acid A mixture of 8.5 g of methyl trans-4-[2-(5,8-dimethyl-6-methoxy-2-naphthyl)-propenyl]-benzoate in 100 cm³ of ethanol and 100 cm³ of 6 N potassium hydroxide solution is stirred under an inert atmosphere, with exclusion of light, at a temperature of about 60° C. for 4 hours. Thereafter, when it has reached ambient temperature, the mixture is acidified by adding 5 N hydrochloric acid. The expected acid precipitates and is filtered off, dried and then recrystallised from tetrahydrofuran. 6 g of trans-4-[2-(5,8-dimethyl-6-methoxy-2-naphthyl)-propenyl]-benzoic acid are obtained in the form of pale yellow crystals melting at 238° C.

The ¹H nuclear magnetic resonance spectrum at 250 MHz corresponds to the trans-structure.

| Elementary analysis | | | |
|---|---|---|---|
| | C | H | O |
| Calculated for $C_{23}H_{22}O_3$ | 79.74 | 6.40 | 13.85 |
| Found | 79.04 | 6.43 | 13.50 |

EXAMPLE 15

Preparation of N-(4'-hydroxyphenyl)-4-[2-(5,8-dimethyl-6-methoxy-2-naphthyl)-propenyl]-benzamide

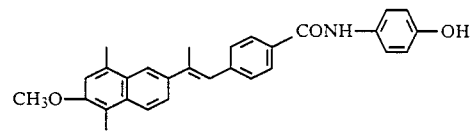

500 mg of trans-4-[2-(5,8-dimethyl-6-methoxy-2-naphthyl)-propenyl]-benzoic acid are dissolved in about 20 cm³ of anhydrous dimethylformamide under an inert atmosphere and with exclusion of light. 300 mg of 1,1'-carbonyldiimidazole are added and the solution is heated at 50° C. for 1 hour; thereafter the reaction mixture is cooled to 0° C. and 200 mg of para-aminophenol are added. The solution is allowed to return to ambient temperature overnight. It is then poured into 200 cm³ of water and extracted with ethyl acetate. The organic phase is washed, dried over magnesium sulphate and concentrated under reduced pressure.

After purification by silica gel chromatography (with a hexane/ethyl acetate eluant), 150 mg of a slightly yellow powder melting from 195° C. onwards are recovered; its ¹H nuclear magnetic resonance spectrum corresponds to the expected structure.

EXAMPLE 16

Preparation of N-(2-hydroxyethyl-oxyethyl)-4-[2-(5,8-dimethyl-6-methoxy-2-naphthyl)-propenyl]-benzamide

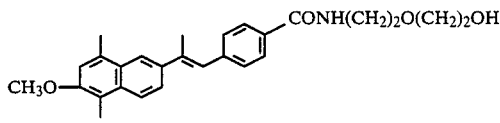

500 mg of trans-4-[2-(5,8-dimethyl-6-methoxy-2-naphthyl)-propenyl]-benzoic acid are dissolved in about 20 cm$^3$ of anhydrous dimethylformamide under an inert atmosphere, and with exclusion of light.

300 mg of 1,1'-carbonyldiimidazole are added and the solution is heated at 50° C. for 1 hour; the reaction mixture is then cooled to 0° C. and 250 mg of 2-hydroxyethyloxyethylamine are added. The solution is allowed to return to ambient temperature for one night. It is then poured into 200 cm$^3$ of water. A bulky precipitate, which is difficult to filter, forms. The mixture is extracted with ethyl acetate and the organic phase is washed, dried over magnesium sulphate and concentrated under reduced pressure.

After recrystallisation from a hexane/ethyl acetate mixture, 400 mg of a white powder melting at 134°-136° C. are obtained, of which the $^1$H nuclear magnetic resonance spectrum corresponds to the expected structure.

EXAMPLE 17

Preparation of N-(1-carboxy-3-methylthio-propyl)-4-[2-(5,8-dimethyl-6-methoxy-2-naphthyl)-propenyl]-benzamide (1) Synthesis of N-(1-ethoxycarbonyl-3-methylthio-propyl)-4-[2-(5,8-dimethyl-6-methoxy-2-naphthyl)-propenyl]-benzamide.

500 mg of trans-4-[2-(5,8-dimethyl-6-methoxy-2-naphthyl)-propenyl]-benzoic acid are dissolved in about 20 cm$^3$ of anhydrous dimethylformamide under an inert atmosphere, with exclusion of light. 250 mg of 1,1'-carbonyldiimidazole are added and the solution is heated at 50° C. for 1 hour. It is cooled to 0° C. and 700 mg (2 equivalents) of the hydrochloride of the ethyl ester of L-methionine are added, followed by 0.50 cm$^3$ of anhydrous triethylamine. The mixture is allowed to return to ambient temperature for one night and is then heated to 50° C. for 5 hours. The reaction mixture is poured onto 200 cm$^3$ of water and extracted with ether, and the extract is dried over magnesium sulphate.

Purification over silica gel (eluant: an 8/2 toluene/ethyl acetate mixture) gives 250 mg of slightly yellow crystals which are pure according to HPLC and melt at 92°-95° C. The $^1$H nuclear magnetic resonance spectrum at 60 MHz agrees with the expected structure.

(2) Synthesis of N-(1-carboxy-3-methylthio-propyl)-4-[2-(5,8-dimethyl-6-methoxy-2-naphthyl)-propenyl]-benzamide 150 mg of the ester obtained above are dissolved in 25 cm$^3$ of ethanol, with exclusion of light, 5 cm$^3$ of 6 N KOH are added and the mixture is heated for 30 minutes at 50°-60° C. The alcohol is evaporated and 50 cm$^3$ of water are added. This mixture is extracted with ether. The aqueous phase is acidified and the white precipitate obtained is filtered off.

After drying, 90 mg of a white powder melting at 176°-178° C. are recovered; the material is pure according to HPLC. The $^1$H nuclear magnetic resonance spectrum at 60 MHz agrees with the expected structure.

EXAMPLE 18

Preparation of the compound represented by the formula:

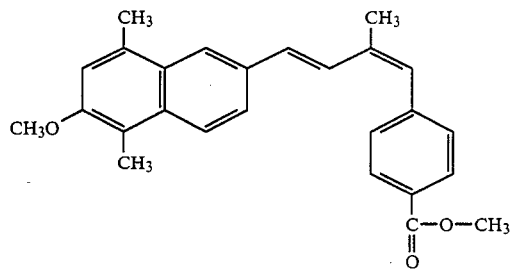

This compound is obtained in accordance with the working method described in Example 9, replacing the 2-naphthaldehyde by 1,4-dimethyl-6-formyl-2-methoxy-naphthalene.

After chromatography over silica gel (eluant: a 99/1 hexane/ethyl acetate mixture), the expected product is obtained in the form of yellow crystals having the following characteristics:

Melting point: 139° C.

| | Elementary analysis | | |
|---|---|---|---|
| | C | H | O |
| Calculated for $C_{26}H_{26}O_3$ | 80.83 | 6.74 | 12.44 |
| Found | 80.72 | 6.82 | 12.51 |

The $^1$H nuclear magnetic resonance spectrum (CDCl$_3$/TMS) agrees with the expected structure.

EXAMPLE 19

An anti-seborrhoea lotion is prepared as follows: 0.2 g of the compound of Example 1 or of Example 11 is added to a solution consisting of 10 cm$^3$ of 95° ethanol and 30 cm$^3$ of polyethylene glycol (molecular weight about 400) containing 20 mg of butylhydroxytoluene.

After dissolving the constituents with stirring, the lotion is applied to the whole of the head of hair. Preferably, a treatment is carried out twice daily. After 15 days' treatment, a satisfactory result is found.

The composition can also be applied to greasy skin.

EXAMPLE 20

A gel is prepared as follows:

| | |
|---|---|
| Compound of Example 8 or of Example 11 | 0.05 g |
| Hydroxypropylcellulose sold by HERCULES under the name of "KLUCEL HF" | 2.00 g |
| Water/ethanol (50/50) sufficient to make | 100 g |

This gel is used once to three times daily for the treatment of acne. After 6 to 12 weeks' treatment, depending on the severity of the case, a satisfactory result is obtained.

EXAMPLE 21

A cream is prepared as follows:

| | |
|---|---|
| Compound of Example 6 | 1 g |
| Mixture of emulsifying lanolin alcohols and refined hydrocarbon-based waxes and oils, sold by B.D.F. Medical under the name of "EUCERIN anhydrous" | 40 g |
| Preservatives as required | |
| Sterile demineralised water sufficient to make | 100 g |

In this cream, the 1% of the compound of Example 6 can be replaced by 0.1% of the compound of Example 14.

In this way, a nonionic suspension constituting a cream is obtained in both cases. These creams, used for the treatment of psoriasis by application once to three times daily, give good results within a period of 30 days.

EXAMPLE 22

An unguent is prepared as follows:

| | |
|---|---|
| Compound of Example 7 or of Example 11 | 0.005 g |
| Polyethylene glycol (molecular weight 400) | 60 g |
| Polyethylene glycol (molecular weight 4,000) | 25 g |
| Vaseline oil sufficient to make | 100 g |

A water-removable unguent is thus obtained. This preparation, used on skin affected by ichthyosis, gives good results.

EXAMPLE 23

A powder is prepared as follows:

| | |
|---|---|
| Compound of Example 5, 12, 13, 14, or 17 | 0.001 g |
| Corn starch | 0.150 g |
| Magnesium stearate | 0.250 g |
| Sucrose sufficient to make | 0.500 g |

The powder is presented in an 0.5 g pill composed of gelatin and titanium dioxide.

One to three pills per day are administered to an adult subject for the treatment of psoriasis and a significant improvement is found after about 30 days.

EXAMPLE 24

An anti-seborrhoea cream is prepared by producing the following formulation:

| | |
|---|---|
| Polyoxyethylene stearate (40 moles of ethylene oxide) sold under the name of "MYRJ 52" by ATLAS | 4 g |
| Mixture of lauric acid esters of sorbitol and sorbitan, polyoxyethylenated with 20 moles of ethylene oxide, sold under the name of "TWEEN 20" by ATLAS | 1.8 g |
| Mixture of glycerol monostearate and distearate sold under the name of "GELEOL" by GATTEFOSSE | 4.2 g |
| Propylene glycol | 10 g |
| Butylhydroxyanisole | 0.01 g |
| Butylhydroxytoluene | 0.02 g |
| Cetyl-stearyl alcohol | 6.2 g |
| Preservatives as required | |
| Perhydrosqualene | 18 g |
| Mixture of triglycerides of caprylic acid and capric acid, sold under the name "MIGLYOL 812" by DYNAMIT NOBEL | 4 g |
| S—Carboxymethyl cysteine | 3 g |
| 99% strength triethanolamine | 2.5 g |
| Compound of Example 11 | 0.05 g |
| Water sufficient to make | 100 g |

In this cream, the compound of Example 11 can be replaced by 1 g of the compound of Example 5 or by 0.05 g of the compound of Example 15 or 16.

EXAMPLE 25

An anti-seborrhoea cream is prepared by producing the following formulation:

| | |
|---|---|
| Polyoxyethylene stearate (40 moles of ethylene oxide) sold under the name of "MYRJ 52" by ATLAS | 4 g |
| Mixture of lauric acid esters of sorbitol and sorbitan, polyoxyethylenated with 20 moles of ethylene oxide, sold under the name of "TWEEN 20" by ATLAS | 1.8 g |
| Mixture of glycerol monostearate and distearate sold under the name of "GELEOL" by GATTEFOSSE | 4.2 g |
| Propylene glycol | 10 g |
| Butylhydroxyanisole | 0.01 g |
| Butylhydroxytoluene | 0.02 g |
| Cetyl-stearyl alcohol | 6.2 g |
| Preservatives as required | |
| Perhydrosqualene | 18 g |
| Mixture of triglycerides of caprylic acid and capric acid, sold under the name of "MIGLYOL 812" by DYNAMIT NOBEL | 4 g |
| 2-Benzylthioethylammonium 5-amino-5-carboxy-3-thiapentanoate | 3 g |
| Compound of Example 11 | 0.05 g |
| Water sufficient to make | 100 g |

In this cream, the compound of Example 11 can be replaced by 1 g of the compound of Example 4.

EXAMPLE 26

An anhydrous lotion is prepared by mixing the following ingredients:

| | |
|---|---|
| Ethanol | 45 g |
| Propylene glycol | 44.85 g |
| Polytetrahydrofuran dimethyl ether | 10 g |
| Compound of Example 14 | 0.01 g |
| Butylhydroxytoluene | 0.05 g |

EXAMPLE 27

A solar-filter gel is prepared by mixing the following ingredients:

| | |
|---|---|
| Ethyl alcohol | 44 g |
| Propylene glycol | 44.15 g |
| Acrylic acid polymer sold under the name of "CARBOPOL 940" by GOODRICH CHEMICAL CO | 1 g |
| 99% strength triethanolamine | 0.5 g |
| Butylhydroxyanisole | 0.01 g |
| Butylhydroxytoluene | 0.02 g |
| Compound of Example 14 | 0.02 g |
| 3,3'-Terephthalylidene-10,10'-dicamphosulphonic acid dihydrate | 0.5 g |
| Purified water sufficient to make | 100 g |

EXAMPLE 28

An anti-acne cream is prepared by mixing the following ingredients:

| | |
|---|---|
| Mixture of glycerol stearates and polyethylene glycol stearates (75 moles) sold under the name of "GELOT 64" by GATTEFOSSE | 15 g |
| Walnut oil polyoxyethylenated with 6 moles of ethylene oxide, sold under the name of "LABRAFIL M 2130 C" by GATTEFOSSE | 8 g |
| Perhydrosqualene | 10 g |
| Colorant as required | |
| Preservatives as required | |
| Perfumes as required | |
| Thioxolone | 0.4 g |
| Polyethylene glycol (molecular weight 400) | 8 g |
| Purified water | 58.5 g |
| Disodium salt of ethylenediaminetetraacetic acid | 0.05 g |
| Compound of Example 14 | 0.05 g |

EXAMPLE 29

A lotion for encouraging new growth of hair is prepared by mixing the following ingredients:

| | |
|---|---|
| Propylene glycol | 20 g |
| Ethanol | 34.92 g |
| Polyethylene glycol (molecular weight 400) | 40 g |
| Water | 4 g |
| Butylhydroxyanisole | 0.01 g |
| Butylhydroxytoluene | 0.02 g |
| Compound of Example 14 or 18 | 0.05 g |
| Minoxidil | 1 g |

EXAMPLE 30

An anti-acne cream is prepared by mixing the following ingredients:

| | |
|---|---|
| Polyoxyethylene stearate (40 moles of ethylene oxide) sold under the name of "MYRJ 52" by ATLAS | 4 g |
| Mixture of lauric acid esters of sorbitol and sorbitan, polyoxyethylenated with 20 moles of ethylene oxide, sold under the name of "TWEEN 20" by ATLAS | 1.8 g |
| Mixture of glycerol monostearate and distearate | 4.2 g |
| Propylene glycol | 10 g |
| Butylhydroxyanisole | 0.01 g |
| Butylhydroxytoluene | 0.02 g |
| Cetyl-stearyl alcohol | 6.2 g |
| Preservatives as required | |
| Polytetrahydrofuran dimethyl ether | 18 g |
| Mixture of triglycerides of caprylic acid and capric acid sold under the name of "MYGLYOL 812" by DYNAMIT NOBEL | 4 g |
| Compound of Example 11 | 0.05 g |
| Water sufficient to make | 100 g |

EXAMPLE 31

An anti-acne gel is prepared by producing the following formulation:

| | |
|---|---|
| Compound of Example 11 | 0.05 g |
| Isopropyl alchol | 40 g |
| Acrylic acid polymer sold under the name of "CARBOPOL 940" by GOODRICH CHEMICAL CO | 1 g |
| 99% strength triethanolamine | 0.6 g |
| Butylhydroxyanisole | 0.01 g |
| Butylhydroxytoluene | 0.02 g |
| Thioxolone | 0.5 g |
| Propylene glycol | 8 g |
| Purified water sufficient to make | 100 g |

EXAMPLE 32

A solar-filter cream is prepared by producing the following formulation:

| | |
|---|---|
| Polyoxyethylene stearate (40 moles of ethylene oxide) sold under the name of "MYRJ 52" by ATLAS | 4.4 g |
| Cetyl-stearyl alcohol | 6.2 g |
| Mixture of glycerol monostearate and distearate sold under the name "GELEOL" by GATTEFOSSE | 4.3 g |
| Butylhydroxyanisole | 0.05 g |
| Butylhydroxytoluene | 0.05 g |
| Xanthane gum | 0.25 g |
| Isopropyl myristate | 4 g |
| Compound of Example 11 | 0.1 g |
| 3,3'-Terephthalylidene-10,10'-dicamphosulphonic acid dihydrate | 2 g |
| 99% strength triethanolamine | 1 g |
| Demineralised water sufficient to make | 100 g |

EXAMPLE 33

A lotion for encouraging new growth of hair is prepared by mixing the following ingredients:

| | |
|---|---|
| Propylene glycol | 13.96 g |
| Polyethylene glycol (molecular weight 300) | 40 g |
| Polyethylene glycol (molecular weight 1,500) | 32 g |
| Isopropanol | 12 g |
| Butylhydroxyanisole | 0.01 g |
| Butylhydroxytoluene | 0.02 g |
| Compound of Example 11 | 0.01 g |
| Minoxidil | 2 g |

EXAMPLE 34

An anti-acne kit comprises two parts:
(a) A gel is prepared by producing the following formulation:

| | |
|---|---|
| Ethyl alcohol | 48.4 g |
| Propylene glycol | 50 g |
| Acrylic acid polymer sold under the name of "CARBOPOL 940" by GOODRICH CHEMICAL CO | 1 g |
| Diisopropanolamine, 99% pure | 0.3 g |
| Butylhydroxyanisole | 0.05 g |
| Butylhydroxytoluene | 0.05 g |
| α-Tocopherol | 0.1 g |
| Compound of Example 11 | 0.1 g |

In this part, the compound of Example 11 can be replaced by that of Example 14.

(b) A gel is prepared by producing the following formulation:

| | |
|---|---|
| Ethyl alcohol | 5 g |
| Propylene glycol | 5 g |
| Disodium salt of ethylenediaminetetraacetic acid | 0.05 g |
| Acrylic acid polymer sold under the name of "CARBOPOL 940" by GOODRICH CHEMICAL CO | 1 g |
| 99% strength triethanolamine | 1 g |
| Sodium lauryl-sulphate | 0.1 g |
| Purified water | 75.05 g |
| 25% strength hydrated benzoyl peroxide | 12.8 g |

The two gels are mixed at the time of use, in equal parts by weight.

We claim:

1. A compound corresponding to the general formula (II)

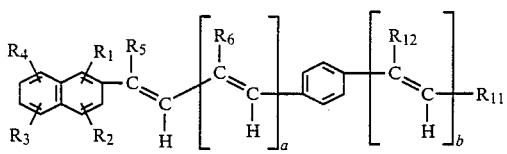

or an isomer or salt thereof, in which formula:

a and b are independently 0 or 1, $R_1$, $R_2$, $R_3$ and $R_4$, which may be present on one or other of the rings or on both simultaneously, independently represent a hydrogen atom, a linear or branched $C_1$-$C_6$-alkyl radical or a $C_1$-$C_4$-alkoxy radical, $R_6$ represents a $C_1$-$C_6$-alkyl radical, $R_5$ and $R_{12}$ independently represent a hydrogen atom or a $C_1$-$C_6$-alkyl radical, with the proviso that $R_5$ cannot represent hydrogen if $a=b=0$ and $R_{11}$ represents a —$COR_9$ group, in which $R_9$ represents (a) a hydrogen atom, a $C_1$-$C_6$-alkyl radical, an amino radical, an optionally substituted arylamino radical or optionally substituted benzylamino radical, a heterocyclic amino radical, a $C_1$-$C_6$-alkylamino radical, or a di($C_1$-$C_6$)alkylamino radical, the alkyl chains of said alkylamino or dialkylamino radicals being optionally substituted by one or more hydroxyl groups and/or contain a chain hetero-atom, the group —$COR_9$, where it is an amide group, moreover optionally being the amide group of an aminoacid or glucosamine, or (b) an $OR_{10}$ radical, where $R_{10}$ represents a hydrogen atom, a $C_1$-$C_6$-alkyl radical, a monohydroxy or polyhydroxy-$C_2$-$C_6$-alkyl radical or a substituted or unsubstituted aryl or benzyl radical, or $OR_{10}$ is derived from a sugar of formula $R_{10}OH$, and $R_{11}$ can also, if b=0, represent a hydroxyl radical, a $C_1$-$C_4$-alkoxy radical, a $C_1$-$C_6$-alkyl radical, a $C_1$-$C_6$-alkylthio radical, a $C_1$-$C_6$-alkylsulphinyl radical, a $C_1$-$C_6$-alkylsulphonyl radical or a sulphonamide radical of the formula (III)

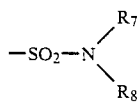

where $R_7$ represents a $C_1$-$C_6$-alkyl radical and $R_8$ either a hydrogen atom or a $C_1$-$C_6$-alkyl radical, and $R_{11}$ can also represent a radical of the formula (IV)

—$CH_2OR_8$ (IV)

in which formula $R_8$ is as defined above.

2. A compound according to claim 1, in which $R_1$ to $R_{12}$ independently represent a methyl, ethyl, isopropyl, butyl or t-butyl radical.

3. A compound according to claim 1, in which $R_9$ and $R_{10}$ independently represent a phenyl radical optionally substituted by a halogen atom, a hydroxyl group or a $C_1$-$C_6$-alkoxy group.

4. A compound according to claim 1 which possesses at least one acid group in the form of a salt of zinc, an alkali metal or alkaline-earth metal or an organic amine or possesses at least one amine group, which is in the form of a salt of an inorganic or organic acid.

5. A compound according to claim 1, in which $R_{11}$ represents —$COR_9$ with $R_9$ representing an optionally substituted arylamino, amino, alkylamino or dialkylamino radical or the radical —$OR_{10}$, $R_{10}$ being as defined in claim 1 or an isomer or an acid salt thereof.

6. A compound according to claim 1, which corresponds to the formula (A)

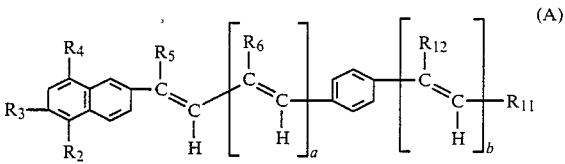

in which $R_5$, $R_6$, $R_{12}$, a and b are defined as in claim 1, $R_3$ denotes a $C_1$-$C_4$-alkoxy radical, $R_2$ and $R_4$ each independently represent a $C_1$-$C_4$-alkyl radical and $R_{11}$ denotes the —$OR_{10}$ radical, $R_{10}$ being defined as in claim 1, or $R_{11}$ denotes —$COR_9$, $R_9$ representing an amino radical, an optionally substituted arylamino or benzylamino radical, a heterocyclic amino radical, an amino acid or glucosamine radical, or an alkylamino or dialkylamino radical, the alkyl chain of said alkylamino and dialkylamino radicals having from 1 to 6 carbon atoms and being optionally substituted by one or more hydroxyl groups and or contain a chain hetero-atom.

7. Process for the preparation of a compound defined in claim 1 which comprises reacting an aldehyde OCHR, in a basic medium, with a substituted or unsubstituted 2-(1'-triphenylphosphonium-alkyl)-naphthalene salt of formula:

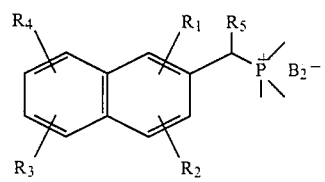

R representing the substituent chain of the formula (V)

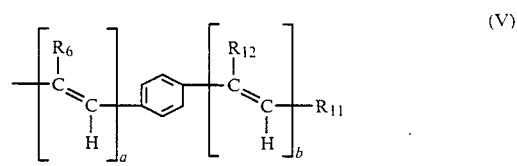

where $R_6$, $R_{12}$, $R_{11}$, a and b are as defined in claim 1.

8. Process for the preparation of a compound as defined in claim 1 which comprises reacting a 2-acylnaphthalene of the formula (VI)

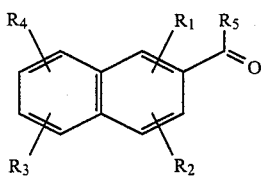 (VI)

with a phosphonate derivative of the formula (VII)

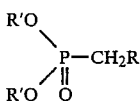 (VII)

or with a triphenylphosphonium salt of the formula (VIII)

$$R-CH_2-P^+(C_6H_5)_3X^-$$ (VIII)

in which formula $R_1$, $R_2$, $R_3$, $R_4$ and $R_5$ are as defined in claim 1, R representing the substituent chain of the formula (V)

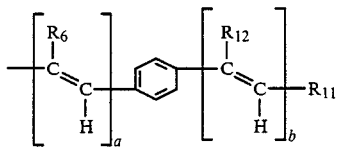 (V)

where $R_6$, $R_{12}$, $R_{11}$, a and b are as defined in claim 1, x represents a halogen atom and R' represents a $C_1$–$C_4$-alkyl radical.

9. A medicinal composition which comprises a pharmaceutically effective amount of at least one compound as defined in claim 1 in a pharmaceutically acceptable base.

10. A composition according to claim 9, suitable for topical use, the concentration of said compound's being from 0.0005% to 2% by weight.

11. A composition according to claim 10 in which the concentration of said compound's is 0.002% to 1% by weight.

12. A composition according to claim 10 which is in the form of an unguent, a gel, a cream, an ointment, a powder, a dyeing composition, a solution, a suspension, an emulsion, a lotion, a spray, an adhesive patch or an impregnated pad.

13. A composition according to claim 9, suitable for enteral use.

14. A composition according to claim 13 suitable for oral use.

15. A composition according to claim 9, which is in the form of a solution or suspension suitable for parenteral use.

16. A composition according to claim 15, which contains from 0.01 to 1 mg of said compound(s) per ml of solution or suspension.

17. A composition according to claim 9, suitable for ocular use.

18. A composition according to claim 9 in which the pharmaceutically acceptable base comprises at least one product selected from the group consisting of water, gelatin, lactose, starch, talc, liquid petrolatum, gum arabic, a polyalkylene glycol, magnesium stearate, diluent, solvent and thickener.

19. A cosmetic composition which contains a cosmetically effective amount of at least one compound as defined in claim 1, in a cosmetically acceptable base.

20. A composition according to claim 19, suitable for application to the skin or hair.

21. A composition according to claim 20 in which the said compound(s) is/are present at a concentration of 0.0005 to 2% by weight.

22. A composition according to claim 21 in which the said compound(s) is/are present at a concentration of 0.01 to 1% by weight.

23. A composition according to claim 19, which is in the form of a lotion, gel, cream, soap or shampoo.

24. A composition according to claim 9, which contains at least one additive selected from the group consisting of a moisturising agent, anti-seborrhoea agent or anti-acne agent, antibiotic, an agent which encourages fresh growth of hair, anti-inflammatory agent, carotenoid, anti-psoriasis agent, flavouring, preservative, stabilizer, moisture regulator, pH regulator, osmotic pressure modifier, emulsifier, UV-A or UV-B filter or antioxidant.

25. A method of treating a patient with a dermatological condition relating to a keratinisation disorder or a dermatological condition which involves an inflammatory or immuno-allergic component which comprises administering to the patient at least one compound as defined in claim 1.

26. A compound having the formula

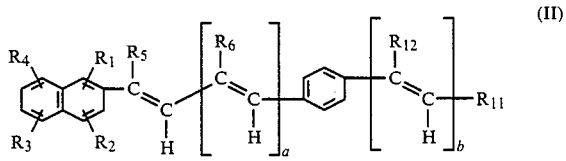 (II)

or an isomer or salt thereof, wherein a and b each independently are 0 or 1, $R_1$, $R_2$, $R_3$ and $R_4$, which may be present on one or the other of the rings, or on both rings simultaneously, each independently represent hydrogen, linear or branched alkyl having 1-6 carbon atoms or alkoxy having 1-4 carbon atoms, $R_6$ represents alkyl having 1-6 carbon atoms, $R_5$ and $R_{12}$ each independently represent hydrogen or alkyl having 1-6 carbon atoms, with the proviso that $R_5$ cannot represent hydrogen when a=b=0, and $R_{11}$ represents —$COR_9$ wherein $R_9$ represents (a) hydrogen; alkyl having 1-6 carbon atoms; amino; arylamino; arylamino substituted by hydroxy, halogen or alkoxy having 1-6 carbon atoms; benzylamino; benzylamino substituted by hydroxy, halogen or alkoxy having 1-6 carbon atoms; alkylamino wherein the alkyl moiety has 1-6 carbon atoms; alkylamino wherein the alkyl moiety has 1-6 carbon atoms and is substituted by one or more hydroxy groups; alkylamino wherein the alkyl moiety has 1-6 carbon atoms and contains a chain heteroatom; alkyl amino wherein the alkyl moiety has 1-6 carbon atoms and is substituted by one or more hydroxy groups and contains a chain heteroatom; dialkyl amino wherein the alkyl moiety contains 1-6 carbon atoms; dialkylamino wherein the alkyl moiety has 1-6 carbon atoms and is substituted by one or more hydroxy groups; dialkylamino wherein the alkyl moiety has 1-6 carbon atoms and contains a chain heteroatom; dialkylamino wherein the alkyl moiety has 1-6 carbon atoms and is substituted by one or more hydroxy groups and contains a chain heteroatom; the —$COR_9$ group, when it is an amide, is optionally the amide group of an amino acid or glucosamine, or (b) $OR_{10}$ wherein $R_{10}$ represents hydrogen; alkyl having 1-6 carbon atoms; monohydroxyalkyl wherein the alkyl moiety has 2-6 carbon atoms; polyhydroxyalkyl wherein the alkyl moiety has 2-6 carbon atoms; aryl; aryl substituted by hydroxy, halogen or alkoxy having 1-6 carbon atoms; benzyl; or benzyl substituted by hydroxy, halogen or alkoxy having 1-6 carbon atoms; or $OR_{10}$ is derived from a sugar of the formula $R_{10}OH$, and $R_{11}$ can also represent, when b=0, hydroxy, alkoxy having 1-4 carbon atoms, alkyl having 1-6 carbon atoms, alkylthio wherein the alkyl moiety has 1-6 carbon atoms, alkylsulphinyl wherein the alkyl moiety has 1-6 carbon atoms, alkylsulphonyl wherein the alkyl moiety has 1-6 carbon atoms or sulphonamide having the formula

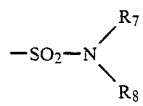

wherein $R_7$ represents alkyl having 1-6 carbon atoms and $R_8$ represents hydrogen or alkyl having 1-6 carbon atoms and $R_{11}$ can also represent —$CH_2OR_8$ wherein $R_8$ has the meaning given above.

27. The compound of claim 26 wherein $R_{11}$ represents —$COR_9$ wherein $R_9$ represents arylamino; arylamino substituted by hydroxy, halogen or alkoxy having 1-6 carbon atoms; amino; alkylamino or dialkylamino, or —$OR_{10}$ wherein $R_{10}$ is defined in claim 26; or an isomer or acid salt thereof.

28. The compound of claim 26 having the formula

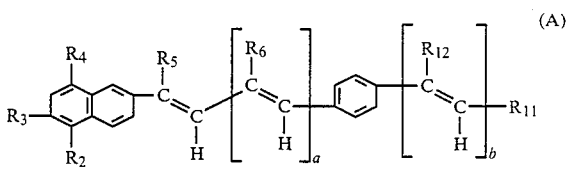

wherein $R_5$, $R_6$, $R_{12}$, a and b have the meanings given in claim 26, $R_3$ represents alkoxy having 1-4 carbon atoms, $R_2$ and $R_4$ each independently represent alkyl having 1-4 carbon atoms, and $R_{11}$ represents —$OR_{10}$ wherein $R_{10}$ has the meaning given in claim 26 or $R_{11}$ represents —$COR_9$ wherein $R_9$ represents amino; arylamino; arylamino substituted by hydroxy, halogen or alkoxy having 1-6 carbon atoms; benzylamino; benzylamino substituted by hydroxy, halogen or alkoxy having 1-6 carbon atoms; amino acid or glucosamine radical; alkylamino wherein the alkyl moiety has 1-6 carbon atoms; alkylamino wherein the alkyl moiety has 1-6 carbon atoms and is substituted by one or more hydroxy groups; alkylamino wherein the alkyl moiety has 1-6 carbon atoms and contains a chain heteroatom; alkylamino wherein the alkyl moiety has 1-6 carbon atoms and is substituted by one or more hydroxy groups and contains a chain heteroatom; dialkylamino wherein the alkyl moiety has 1-6 carbon atoms; dialkylamino wherein the alkyl moiety has 1-6 carbon atoms and is substituted by one or more hydroxy groups; dialkylamino wherein the alkyl moiety has 1-6 carbon atoms and contains a chain heteroatom; and dialkylamino wherein the alkyl moiety has 1-6 carbon atoms and is substituted by one or more hydroxy groups and contains a chain heteroatom.

29. The compound of claim 1 which is trans-4-[2-(5,8-dimethyl-6-methoxy-2-naphthyl)-propenyl]-benzoic acid.

* * * * *